(12) United States Patent
Ikeda et al.

(10) Patent No.: US 7,368,052 B2
(45) Date of Patent: May 6, 2008

(54) PROCESS FOR DISCHARGING AND TRANSFERRING FLUIDIZED PARTICLES

(75) Inventors: Yoneichi Ikeda, Kamakura (JP); Yuichiro Fujiyama, Yokohama (JP)

(73) Assignee: Nippon Mitsubishi Oil Corporation, Tokyo (JP)

( * ) Notice: Subject to any disclaimer, the term of this patent is extended or adjusted under 35 U.S.C. 154(b) by 568 days.

(21) Appl. No.: 10/087,238

(22) Filed: Mar. 1, 2002

(65) Prior Publication Data

US 2002/0131911 A1     Sep. 19, 2002

(30) Foreign Application Priority Data

Mar. 15, 2001   (JP)   .............. 2001-073839

(51) Int. Cl.
  *C10G 9/32*   (2006.01)
  *C10G 35/16*   (2006.01)
(52) U.S. Cl. ............... 208/127; 208/126; 208/148; 208/153; 208/163; 208/176
(58) Field of Classification Search ............... 422/141, 422/139, 145; 208/153, 156, 176, 164
See application file for complete search history.

(56) References Cited

U.S. PATENT DOCUMENTS 3,409,542 A * 11/1968 Molstedt .................. 208/127
3,735,498 A *  5/1973 Suzukawa et al. ............ 34/370
4,693,808 A     9/1987 Dewitz

FOREIGN PATENT DOCUMENTS

JP         01-198688         8/1989

* cited by examiner

*Primary Examiner*—Tam M. Nguyen
(74) *Attorney, Agent, or Firm*—Panitch Schwarze Belisario & Nadel LLP

(57) ABSTRACT

A process is disclosed for discharging and transferring upwardly fluidized particles from a dense fluidizing layer forming section to a high-velocity transferring section having a diameter which is smaller than that of the dense fluidizing fluidized layer forming section, wherein at least one intermediate cylindrical section is provided between the dense fluidizing fluidized layer forming section and the high-velocity transferring section. The process can decrease the degree of changes in the amount of particles to be discharged from the dense fluidizing layer forming section and transferred by the riser, thereby proving a stable and uniform transfer of the fluidized particles.

5 Claims, 1 Drawing Sheet

PROCESS FOR DISCHARGING AND TRANSFERRING FLUIDIZED PARTICLES

BACKGROUND OF THE INVENTION

1. Field of the Invention

This invention relates to a process for discharging and transferring fluidized particles from a dense fluidizing layer forming section to a high-velocity transferring section having a diameter smaller than the dense fluidizing layer forming section.

2. Description of the Prior Art

Conventionally, fluidizing layers (beds) have been widely used in the treatments or chemical reactions of particles or gas. Fluidizing layers vary in form, and particularly fluidizing layers which circulate fluidized particles through the outer equipment have been applied to a reaction such as a petroleum catalytic cracking process which requires the continues regeneration of catalyst.

In order to improve the operation stability and reaction result of a system using such a circulating fluidizing layer, it is necessary to continuously circulate the fluidizing layer in a stable manner. For that purpose, it is important to permit the smooth continuous discharge, transfer and supply of particles from the fluidized layer. In recent years, there has been proposed a high-performance petroleum catalytic cracking process known as downflow type fluid catalytic cracking process hereinafter referred to as "downer type FCC". In this process, the catalyst flows downwardly through the reactor. Therefore, thereafter it is necessary to transfer the catalyst upwardly while being regenerated. The present invention is the most effective when being applied to such a system.

Description of the Prior Art

Typical examples of conventional downer type FCC reactors are disclosed in Japanese Patent Publication Nos. 2,523, 325 and 2,590,009. In these methods, the catalyst regenerator wherein a dense fluidizing layer is formed has an upper portion which is conical and connected to a high-velocity transferring section hereinafter referred to as "riser", thereby making it possible to transfer the catalyst up to a height which is required by the downer, i.e., down flow reactor as well as continuous regeneration of the catalyst. In such systems, sufficient contact time required for the regeneration in the dense fluidizing layer can be ensured and the regenerated catalyst can be transferred and discharged by the riser without additional gas flow and mechanical operation.

However, although these systems excel in principle, they can not avoid the amount of particles to be transferred from the dense fluidized layer to the riser from varying due to the changes of the fluidizing state in terms of time and position which are peculiar thereto. As a result, there occur pressure loss in the riser and changes in the residence time of particles in the regenerator, leading to changes in the results of the treatments in the decomposition section and the catalyst- and adhered oil removing sections. These factors cause the decrease of the total reaction results and unstable operation.

SUMMARY OF THE INVENTION

An object of the present invention is to provide a process which can achieve the stable and uniform transfer of particles by decreasing the degree of changes in the amounts of particles to be discharge from the dense fluidized layer and transferred by the riser and is simple in structure and hard to have troubles such as wear and malfunction of the apparatus.

Particularly when the process of the present invention is applied to a circulating fluidizing layer system such as a downer-type FCC, the operation is stabilized with the regeneration and decomposition steps sufficiently progressing, leading to an improvement in the reaction result.

According to the present invention, there is provided a process of discharging and transferring upwardly fluidized particles from a dense fluidizing layer forming section to a high-velocity transferring section having a diameter which is smaller than the diameter of the dense fluidizing fluidized layer forming section wherein at least one intermediate cylindrical section is provided between the dense fluidizing fluidized layer forming section and the high-velocity transferring section.

According to another aspect of the present invention, the diameter of the intermediate cylindrical section is preferably ⅓ to ⅔ times that of the dense fluidizing layer forming section.

According to another aspect of the present invention, the height of the intermediate cylindrical section is preferably 1 to 6 times the diameter thereof.

According to another aspect of the present invention, the intermediate cylindrical section has preferably truncated cone ends connected to the dense fluidized fluidizing layer forming section and the high-velocity transferring section, respectively.

According to another aspect of the present invention, the truncated cone end directly connected to the dense fluidized fluidizing layer forming section has preferably an elevation elevated angle of 40 to 80°.

According to another aspect of the present invention, preferably only one intermediate cylindrical section is provided.

According to another aspect of the present invention, the average particle size of the fluidized particles is preferably 30 to 90 µm, and the gas superficial speed for fluidization is preferably 0.3 to 1.2 m/s in the dense fluidizing layer forming section and 3 to 30 m/s in the high-velocity transferring section.

DETAILED DESCRIPTION OF THE INVENTION

1) Fluidized State and Selection Thereof

Figure 1:
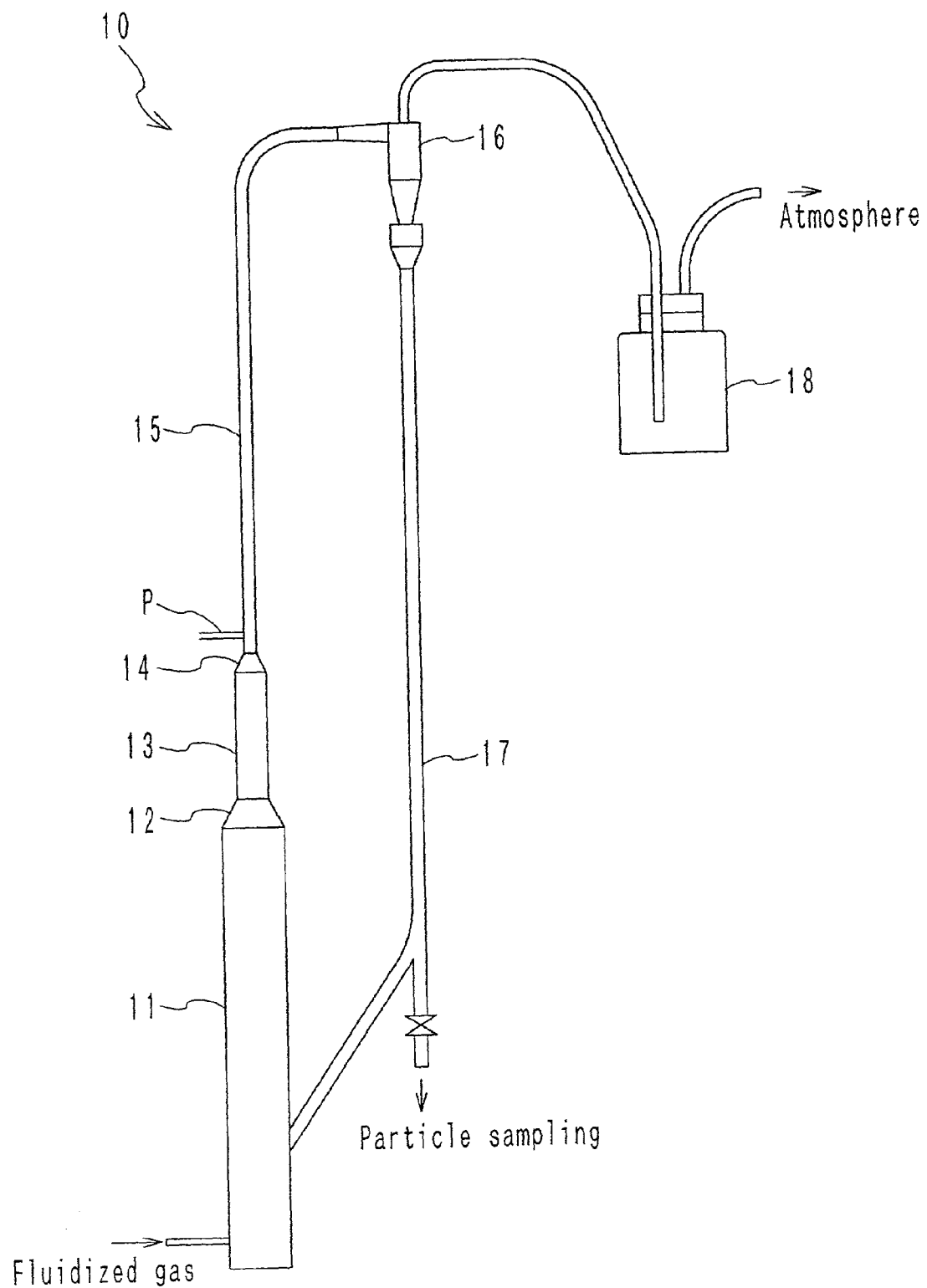
FIG. 1 is a flow diagram of the apparatus used in the example.

For a catalytic reaction, a uniform fluidizing state where gas and particles contact well can be obtained using finely divided particles having an average particle size of 30 to 90 µm, and preferably 50 to 70 µm. When such finely divided particles are used and the superficial velocity of fluidizing gas is 0.3 to 1.2 m/s, and preferably 0.4 to 1 m/s, a dense fluidizing layer with a relatively large density is usually formed. Such a dense fluidizing layer is mostly distinguished from a bubble fluidizing layer and a turbulent fluidizing layer.

When the gas superficial velocity is 3 to 30 m/s, and preferably 5 to 20 m/s, a high-velocity transferring layer with a relatively small density is formed in which the particles are transferred at a higher velocity. This is a so-called sparsely transferring layer, air current transfer, or riser. The dense fluidizing layer is suitable for a regeneration reaction which is expected to be carried out at a constant temperature for a long period of time because the temperature distribution of the fluidizing bed is uniform and the residence time for particles can be prolonged. Since in the high-velocity transferring layer, particles are transferred at high velocity together with gas, the layer is suitable for transferring particles. The present invention is based on the selection and combination of these layers.

2) Transferring of Particles and Adjustment Thereof

Higher the gas superficial velocity is, the amount of particles to be discharged and transferred from the dense fluidizing layer is larger. Furthermore, the higher the dense fluidizing layer and thus shorter the upper space (hereinafter referred to as freeboard) of the dense fluidizing layer forming section, the amount is also larger. As mentioned above, since the gas superficial velocity is limited for the formation of the dense fluidizing layer, it is necessary to make the freeboard short by increasing the height of the fluidizing layer so as to increase the amount of particles to be transferred. Generally, since in the conventional FCC, the circulating fluidizing layer needs a relatively large amount of catalyst, the freeboard must be decreased so as to discharge the large amount of catalyst.

When observing the surface of a dense fluidizing layer, it is non-uniform in terms of time and position. Furthermore, clusters of particles jump out from the surface when bubbles rising through the layer rapture. Thereafter, the clusters break up, and then the descending of a part thereof and the rising of the remaining clusters are repeated. In a shorter freeboard, the clusters can not break up completely even though the upper portion of the dense fluidizing layer forming section is formed into truncated cone. Therefore the cluster can pass through the upper portion and reached the high-velocity transferring section. As a result, the amount of transferred particles varies and pressure loss occurs.

3) Features of the Present Invention

The present invention provides a process of discharging and transferring upwardly fluidized particles from a dense fluidizing layer forming section to a high-velocity transferring section having a diameter which is smaller than that of the dense fluidizing fluidized layer forming section, characterized in that at least one intermediate cylindrical section is provided between the dense fluidized fluidizing layer forming section and the high-velocity transferring section.

In the present invention, the intermediate cylindrical section is not limited to a normal cylindrical shape of which upper and lower portions have the same diameter and encompasses a substantially cylindrical shape whose upper and lower portions have a different diameter. That is, the intermediate cylindrical section may be those whose lower portion has a larger diameter than the upper portion or whose elevation angle is 85° or greater. Furthermore, the intermediate cylindrical section includes any cylindrical shape whose center portion is bulged or constricted.

The diameter of the intermediate cylindrical section is preferably ⅓ to ⅔ times larger, and more preferably ⅖ to ⅗ times larger than the diameter of the dense fluidizing layer forming section. Using an intermediate cylindrical section with such a size in relation to the dense fluidizing layer forming section, the gas velocity in the intermediate section reaches about 3 to 6 times faster velocity than the gas superficial velocity in the dense fluidizing layer and is sufficient to break up the above-mentioned clusters. Furthermore, the diameter of the intermediate cylindrical section is preferably 1.2 to 7 times larger, and more preferably 1.5 to 5 times larger than the diameter of the high-velocity transferring section.

The height of the intermediate cylindrical section is preferably 1 to 6 times, and more preferably 1.5 to 4 times the diameter thereof. The height which is less than 1 time the diameter is insufficient to break up the clusters and thus can not make the particles disperse uniformly in the gas, possibly resulting in the failure to obtain the good results to be achieved by the present invention. The height which is more than 6 times the diameter can not exhibit significant changes in effect and merely makes the apparatus larger. Therefore, it is disadvantageous in terms of cost.

A plurality of the intermediate cylindrical sections may be provided. However, a plurality of the intermediate cylindrical sections only make the structure of the apparatus complicated and exhibit almost no significant change in the effect achieved thereby. Therefore, it is preferred that one intermediate cylindrical section be provided.

The intermediate cylindrical section preferably has the truncated cone ends connected to the dense fluidizing layer forming section and the high-velocity transferring section, respectively.

No particular limitation is imposed on the elevation angle of the truncated cone ends which, however, is preferably 40 to 80°. Particularly, the elevation angle of the lower truncated cone end which is closer to the dense fluidizing layer forming section is preferably 40 to 80°, and more preferably 45 to 75°. The elevation angle of less than 40° is not worth forming the end to be truncated and possibly make the particles separate easily from the gas flow. The elevation angle of larger than 80° merely increases the height of the truncated end and can not obtain the effect as better as expected, resulting in an increase in the height of the apparatus which is disadvantageous in terms of cost.

The elevation angle of the truncated end to be connected to the dense fluidizing layer forming section may be the same or different from that of the truncated end to be connected to the high-velocity transferring section.

Each of the truncated ends may be formed with one truncated portion with a single elevation angle or may be formed with a plurality of truncated portions each having a different elevation angle. However, the former is preferred.

In the process of the present invention, clusters rising through the lower truncated end break up while rising through the intermediate cylindrical section such that the particles rise with uniformly dispersed in the gas. Therefore, since the inventive process makes it possible to decrease the degree of changes in the amounts of particles to be discharged from the dense fluidizing layer forming section and transferred by the riser can be decreased, the process is almost free from changes in the amount of particles to be transferred through the high-velocity transferring section and from pressure loss, thereby being able to achieve a stable particle transfer.

The present invention need substantially no structural object in the apparatus and is, therefore, free from troubles such as wear of parts in the apparatus and crush of particles.

The present invention is now described in more detail with reference to the annexed drawing.

EXAMPLE

1) Experimental Apparatus

The experimental apparatus had two truncated portions, and each of the parts were made of a transparent plastic so as to be able to observe the inside thereof. Pressure change in the lower portion of the riser was measured with a strain gauge.

FIG. 1 shows a flow of the apparatus.

The specifications of each part of the apparatus are as follows.

Dense fluidizing forming section (11)
    Diameter $D_\gamma$=5.0 cm, Height $H_\gamma$=30 m Lower truncated portion (12)
    Elevation angle $\theta_1$=60°, Height $H_{c1}$=2.0 cm Intermediate cylindrical section (13)
    Diameter $D_p$=2.6 cm, Height $H_p$=10 cm $H_p/D_p$=3.8

Upper truncated portion (14)
    Elevation angle $\theta_2$=60°, Height $H_{c2}$=1.3 cm Riser (5)
    Diameter $D_R$=1.1 cm, Height $H_R$=1.5 m 2) Experimental Conditions The fluidized catalyst was a normal FCC catalyst with an average particle diameter of about 60 μm and a bulk density of 0.827 g/cm³. The fluidizing gas was air supplied at ordinary temperature and atmospheric pressure.

The other conditions are as follows.

Filling amount of the particles $W_s$=325 g

Layer height at rest $L_q$=20 cm

Fluidizing gas flow rate $V_G$=40 L/min

The superficial gas velocities at each part were as follows.

Dense fluidizing layer forming section
    $U_O$=33 cm/s

Intermediate cylindrical section
    $U_P$=1.25 m/s

Riser
    $U_R$=7.0 m/s

3) Experimental Results

Dense fluidizing layer density
    $\rho_f$=0.517 g/cm³

Fluidized layer height
    $L_f$>30 cm

Circulating rate of transferred particles
    $E_s$=$F_s$=4.8 g/s

Average pressure change in the riser
    $\Delta P_R$=78.4 Pa (8 mmaq)

4) Observation Results

It was observed that clusters of particles jumping out from the fluidizing layer collapsed in the freeboard and particles rose through the riser (15) with uniformly dispersed in the gas. It was also observed that no time variation in particle load to the cyclone separator (16) occurred, and no clogging from the separator (16) to the particle down-flow circulating line (17) occurred.

COMPARATIVE EXAMPLE

An experiment was conducted under the same conditions as those of the Inventive Examples using an apparatus whose truncated portion (12) was directly connected to the riser (15) and whose remaining parts were the same as those of the apparatus used in the Inventive Example. As a result, it was observed that the pressure change in the riser was 127.4 Pa (13 mmaq) and increased 1.6 times more than that of the Inventive Example. It was also observed that the collapse of the clusters rising from the fluidizing layer was insufficient, and most of the clusters passed through the truncated portions and reached the riser. Furthermore, it was observed that bulks of particles in the form of highly-dense vertical stripes were transferred, varying in time. Variation in particle load was observed in the cyclone and the following particle down-flow circulating line and clogging occurred frequently.

What is claimed is:

1. A process of discharging and transferring upwardly fluidized particles from a dense fluidizing layer forming section to a high-velocity transferring section having a diameter which is smaller than a diameter of the dense fluidizing layer forming section, wherein at least one intermediate cylindrical section having an elevation angle of 85° or greater is provided between the dense fluidizing layer forming section and the high-velocity transferring section, and wherein an average particle size of the fluidized particles is 30 to 90 μm, and a gas superficial speed for fluidization is 0.3 to 1.2 m/s in said dense fluidizing layer forming section and 3 to 30 m/s in said high-velocity transferring section; and wherein a superficial gas velocity in the at least one intermediate cylindrical section is about 0.9 to 7.2 m/s and a height of said intermediate cylindrical section is 1.5 to 4 times a diameter thereof.

2. The process according to claim 1 wherein a diameter of said intermediate cylindrical section is ⅓ to ⅔ times the diameter of the dense fluidizing layer forming section.

3. The process according to claim 1 wherein said intermediate cylindrical section has truncated cone ends connected to said dense fluidizing layer forming section and said high-velocity transferring section, respectively.

4. The process according to claim 1 wherein the truncated cone end directly connected to said dense fluidizing layer forming section has an elevation angle of 40 to 80°.

5. The process according to claim 1 wherein only one intermediate cylindrical section is provided.

\* \* \* \* \*